United States Patent [19]
Loren

[11] Patent Number: 5,875,788
[45] Date of Patent: Mar. 2, 1999

[54] FIBER BUNDLES

[76] Inventor: Daniel Loren, 96 Prospect Ave., Valhalla, N.Y. 10595

[21] Appl. No.: 771,385

[22] Filed: Dec. 16, 1996

[51] Int. Cl.[6] .................................................. A41G 3/00
[52] U.S. Cl. ............................. 132/53; 132/201; 132/56
[58] Field of Search ................... 132/201, 53, 56; 300/1, 21

[56] References Cited

U.S. PATENT DOCUMENTS

| | | | |
|---|---|---|---|
| 1,199,144 | 9/1916 | Zak | 132/53 |
| 2,697,304 | 12/1954 | Welch | 132/201 |
| 3,032,042 | 5/1962 | Meehan | 132/53 |
| 3,687,752 | 8/1972 | Riordan, Jr. | 132/56 |
| 3,910,291 | 10/1975 | Kim | 132/53 |
| 3,946,606 | 3/1976 | Abrioux et al. . | |
| 3,980,092 | 9/1976 | Garufi . | |
| 4,016,889 | 4/1977 | Cowles | 132/56 |
| 4,061,022 | 12/1977 | Yates . | |
| 4,224,475 | 9/1980 | Hubbard . | |
| 4,392,384 | 7/1983 | Yquel . | |
| 4,474,193 | 10/1984 | Watanabe et al. . | |
| 4,510,951 | 4/1985 | Watanabe et al. . | |
| 4,583,562 | 4/1986 | Stewart . | |
| 4,628,742 | 12/1986 | Golding . | |
| 4,972,718 | 11/1990 | Said et al. . | |
| 5,271,420 | 12/1993 | Park | 132/56 |
| 5,413,124 | 5/1995 | Incando | 132/56 |
| 5,520,203 | 5/1996 | Segerstrom . | |

*Primary Examiner*—Todd E. Manahan

[57] ABSTRACT

Provided herein is a process for producing bundles of fibers useful for testing of various physical properties of said bundles. The bundles include fibers attached to one another at one of their ends by various means, said means employed being selected dependent upon the type of physical testing intended for the fibers. The fibers may be keratin fibers.

10 Claims, 3 Drawing Sheets

FIBER BUNDLES

CROSS REFERENCES TO RELATED APPLICATIONS none

BACKGROUND OF THE INVENTION

1. Technical Field

This invention relates to providing bundles of fibers and particularly to a method for producing bundles of fibers which are to be used in evaluating the physical properties of the fibers. The fibers may be of various composition and include keratin fibers, i.e., human hair.

2. Background Information

The use of fiber products dates back to the earliest times of recorded history. Generally speaking, different fibers have been determined to be useful in a wide range of differing particular applications, the choice of which is dependent upon the physical requirements in each case. Fibrous materials include those of: cotton, hemp, cellulose esters, polyesters, hairs of various mammals including wool and human hair, synthetic fibers including kevlar, nylon, nomex, polyamides, poly acrylates, etc. Examples in which fibers are useful are for clothing, rugs, insulation, composite materials, printed circuitboard prepregs, wigs, etc.

Heretofore, in order to characterize, classify, determine the suitability of various fibrous materials, or test various chemical treatments for their suitability and usefulness thereon a wide range of test methods have been developed. Generally, properties upon which evaluation of fibers are based include intrinsic elongation, damage index, tensile strength, wear characteristics, reactivity or inertness to particular chemical/physical conditions, color change resistance under particular conditions, ease of cleansing, reaction to heat stress, tendency to tangle, and the degree of deviation of these properties exhibited by a treated fiber with respect to virgin fibers under ideal or other laboratory or field test conditions.

Commensurate with the increase in the chemical complexity of treatments applied to various fibrous materials has been witnessed a general need for a more rigidly controlled set of experimental parameters useful for evaluating the usefulness of the various treatments. Part of this need includes providing the fibers to be tested in a fixed form, since free-standing fibers are undesirable in most cases due to the fact that they tend to move about uncontrollably in a random fashion as a result of the various physical manipulations to which they are subjected throughout the various testing procedures.

Accordingly, it has been found desirable to provide a prefabricated swatch of fibers useful to those engaged in the evaluation of said fibers in order to increase reliability of test results, save time, and reduce costs associated with evaluating new products for the various markets.

Hair swatches and bundles of fibers heretofore employed included several strands fixed at their ends, for example, as disclosed in U.S. Pat. Nos. 4,061,022; 4,224,475; 4,392,384; 4,474,193; and 4,583,562, wrapped around a rod as disclosed in U.S. Pat. No. 4,510,951, and as set forth in the prior art patents and literature cited therein.

Thus, a large number of different means for bundling strands of fibers together for a specific application have been seen to develop, and the manner in which the bundles are held together have being specific to their intended application. This means that generally there was no fixed standard in the industry against which all could be compared to as a reference, i.e., each testing lab or facility has had its own "in-house" method of providing a form of the fibers to be tested.

The instant invention provides a set of standard fiber bundle which may be evaluated for a more meaningful comparison of data generated in a particular given test, as well as a more convenient, easy to use, and cost-effective means of carrying out physical testing of fibrous materials.

SUMMARY OF THE INVENTION

In accordance with the foregoing, it may be regarded as an object of the present invention to provide bundles of fibers which enable those engaged in the physical testing of fibrous materials a convenient source of fiber bundles employable in the evaluation of the physical properties of fibers treated with various novel chemical products treatments, or physical conditions. It may also be regarded as an object of this invention to provide a set of standard fiber bundles to the various industries which may be considered as a reference forthwith in those industries.

In accordance with the present invention, the above objects are accomplished by first providing a plurality of fibers of similar length in an essentially flat configuration wherein the individual fibers are positioned adjacent to one another with at least one of the ends of the fibers being aligned with one another. The fibers are then sewn together near their end portions, within about 1 inch of their ends with the stitch running perpendicular to the length of the fibers. Subsequently the ends of the fibers so sewn together along with the end portion of the bundle and are treated with a chemical binding agent which covers, protects, and reinforces the stitched portion, so as to produce an essentially flat bundle or "swatch" of fibers. The swatch thus produced is then suitable for evaluating various fiber treatments.

DESCRIPTION OF PREFERRED EMBODIMENT

Figure 1:
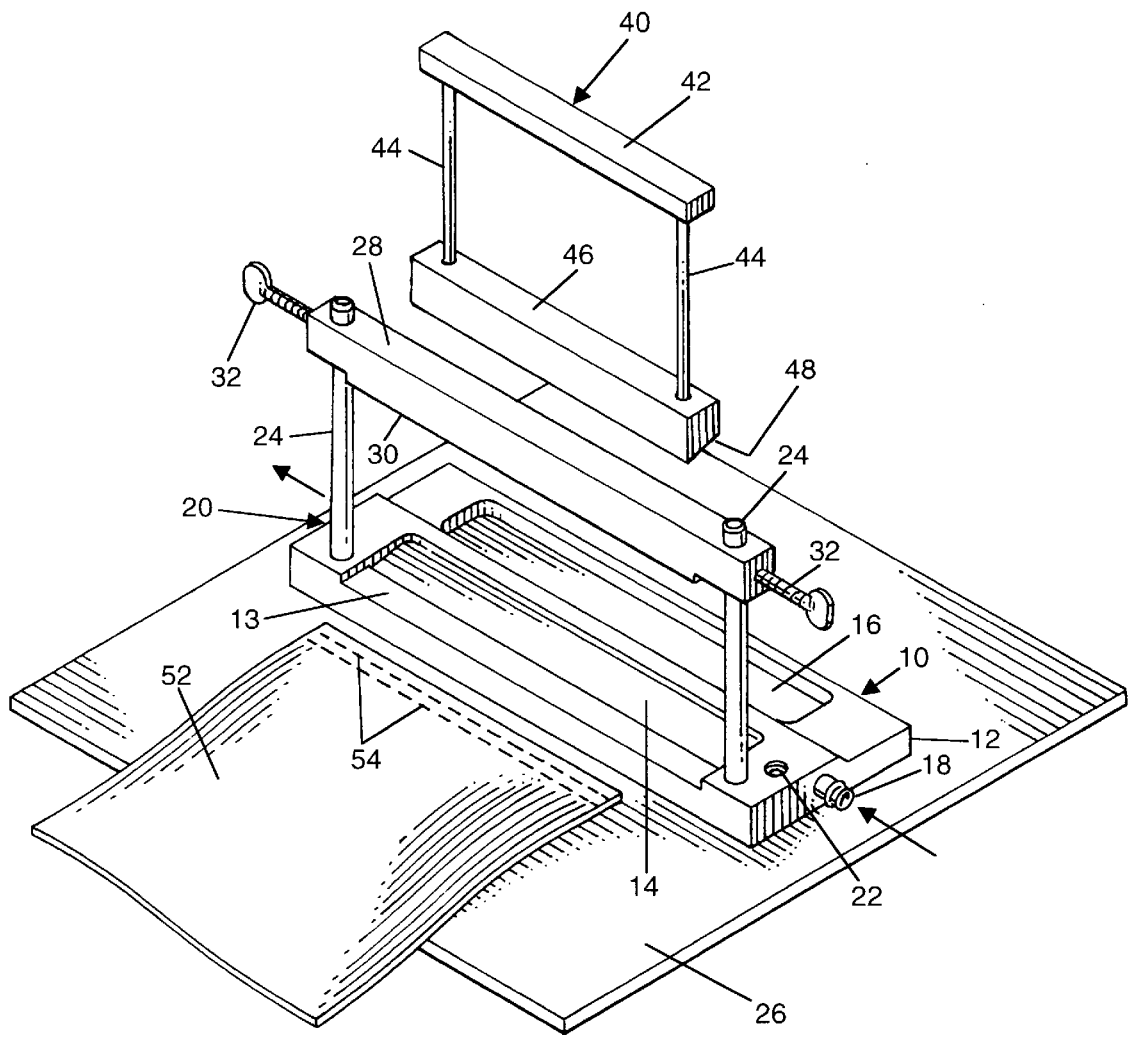
FIG. 1 is a perspective exploded view of the molding device employed herein to form fiber bundles according to this invention, showing the mold housing on its base with a finished bundle of fibers spaced out front, and the press spaced above.

In accordance with this invention, a group of fibers are first formed into a rough bundle by placing the individual strands adjacent to one another and at the desired finished linear density and thickness. The maximum number of fiber strands per unit length which will fit next to one another side by side, owing to the diameter of the fibers, is the maximum linear density. Once this maximum number is reached, addition of more fibers can no longer contribute to the linear number of strands per unit length of the fiber bundle, but will rather contribute towards increasing the thickness of the finished fiber bundle. The most preferable range of the linear density of fibers in a bundle produced according to this invention is between about 50 and 400 strands per centimeter, and the thicknesses of the finished fiber bundle is preferably between about the diameter of a single fiber and 2.5 centimeters, and between about 0.3 centimeters and 2.0 centimeters when the fibers comprise human hair.

The fibers to be treated according to this invention are first cut to the desired length. The desired number of fibers are bundled together and held by the hand of a skilled operator in their desired finished position with all of the fibers being aligned along at least one of their ends.

Next, the fibers are sewn together using preferably a straight stitch, although other stitches are suitable including zig-zag stitches or any other types of stitches commonly employed in the textile industry. The fibers are sewn together in a direction perpendicular to their lengths within about 1 inch and preferably within about 1–10 millimeters from their ends.

Finally, the stitched portion of the fibers is treated with a binding agent which increases the integrity of the stitching to such a degree that normal physical handling does not allow the fiber bundles to distort, move about in a random fashion, or their physical configuration to be compromised in any other way.

The composition of the binding agent with which the fiber bundle is treated after being sewn together is critical to the finished product produced herein. Depending upon the nature of the physical testing to be done on a group of particular fibers, different compositions of binding agent may be employed.

Suitable binding agents for use in this invention include nearly all castable polymeric materials and mixtures thereof, with the proviso that the melting point of the binding agent must be about 10 degrees centigrade higher than the temperature at which the physical testing of the fiber bundles is to take place. Castable polymeric materials include common industrial plastic mixtures which comprise: polyethylene, polypropylene, polyacrylates, polystyrene, substituted polystyrenes, polyurethanes, ABS, nylons, polybutene, natural latex, and mixtures thereof, but may also include other materials known to those of ordinary skill in the chemical arts as simply "polymers" including so-called "hot melt" glue, an example of which is sold in True Value (™) hardware stores, item DT-20mm, 457-033 and its analogs.

By exhaustive experimentation it has been determined that the most preferred binding agent according to this invention comprises a mixture of: 1) a proprietary polymer comprising vinyl acetate sold in the United States by by E.I. Dupont de Nemours known as "Elvax-40"; and 2) natural beeswax, when the fibers to be bundled together comprise human hair. It has been determined that within this embodiment of the invention the most preferable ratio of this proprietary product to natural beeswax is five parts polymer to one part natural beeswax.

The use of additives in the binding agents such as waxes or other plasticizing esters is desirable in order to increase the ease with which the finished bundles are removed from the mold in which they are made, in allowing a quicker cure time thus permitting an increased production throughput and for decreasing the brittleness of the polymeric portion of the finished fiber bundle. Included as useful as additives are plasticizers commonly employed in the polymer industry such as branched esters of phthalic acid, including diisodecylphthalate, and diisononylphthalate, wax, and beeswax.

For purposes of this specification and the appended claims, the term "beeswax" means an ester produced by bees, which upon hydrolysis yields a mixture of mainly straight chain carboxylic acids having between 25 and 29 carbon atoms and straight chain primary alcohols having between 29 and 33 carbon atoms, regardless of the relative percentage content of each alcohol and ester.

Other waxes useful in the place of the beeswax component of the binding agent according to this invention include those waxes which upon hydrolysis yield mainly carboxylic acids and alcohols having greater than about 16 carbon atoms, straight chain or branched, and long chain alcohols, having greater than about 16 carbon atoms, either primary, secondary, or tertiary, straight-chain or branched. For purposes of this invention, the term "wax" means esters of carboxylic acids and alcohols, said acid or alcohol having greater than about 16 carbon atoms, be they straight chain or branched; and in the case of alcohols, primary, secondary, or tertiary.

FIG. 1 depicts the preferable water-cooled molding device useful for producing bundles of fibers according to this invention. In this figure, 26 represents a base portion upon which the mold assembly 10 is mounted by means of fasteners 22. A stitched bundle of fibers is laid into machined recess 13 and is held in stationary position by stabilizing bar 28, said stabilizing bar including a protruding portion 30. The position of the stabilizing bar is maintained by means of thumbscrews 32 which are tightened upon locator rods 24 which are affixed to the base portion. The machined recess 14 is the location at which the stitched ends of the fiber bundle reside when all elements are in their proper position. 12 is a lower-relief section of the mold assembly, and 16 is a catch-basin for any excess binding composition. The mold assembly includes a hollow portion (not shown) between machined recess 14 and catch-basin 16 for passage of coolant liquid. 18 is coolant inlet and 20 is a coolant outlet. 54 is the stitched portion of the fiber bundle, and 52 is the fibers. 40 is the hand-held press bar which comprises a handle 42, support members 44 and pressing portion 46 having an angled portion 48.

Figure 2:
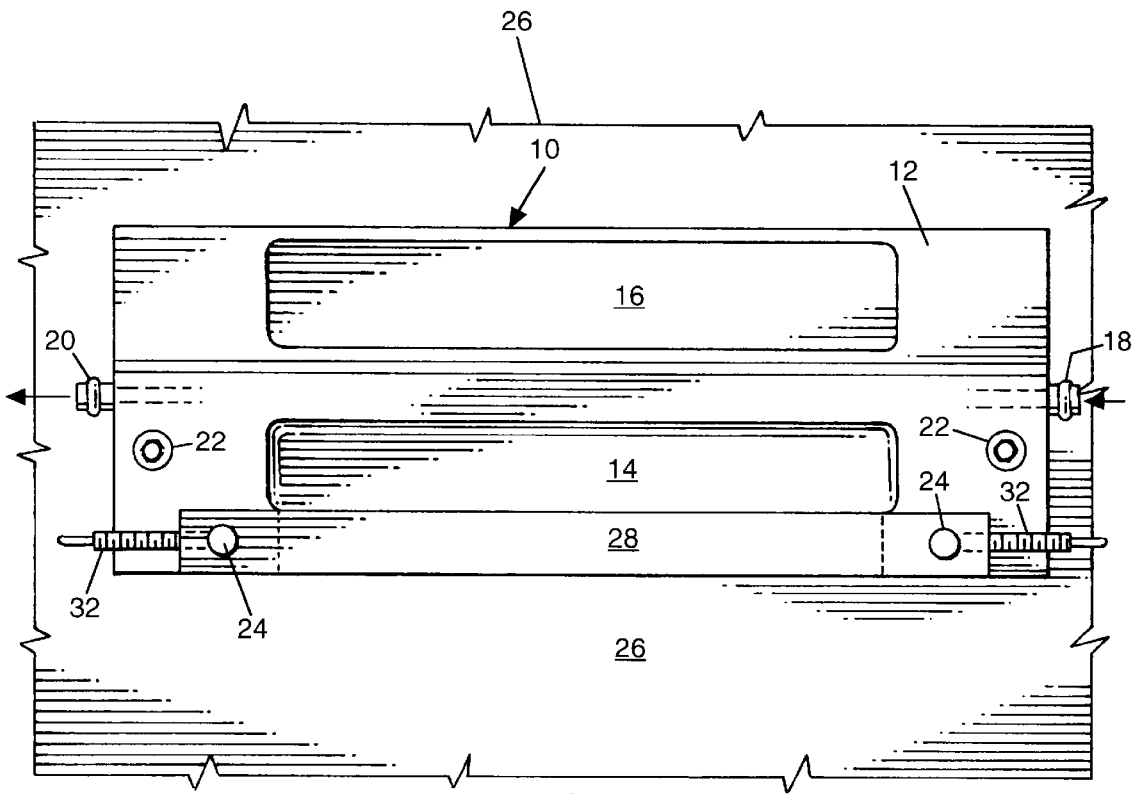
FIG. 2 is a top plan view of the mold used to form the fiber bundles according to this invention.

FIG. 2 is a top plan view of the mold assembly. It shows more clearly the relationship of the locations of the various portions of the mold.

Figure 3:
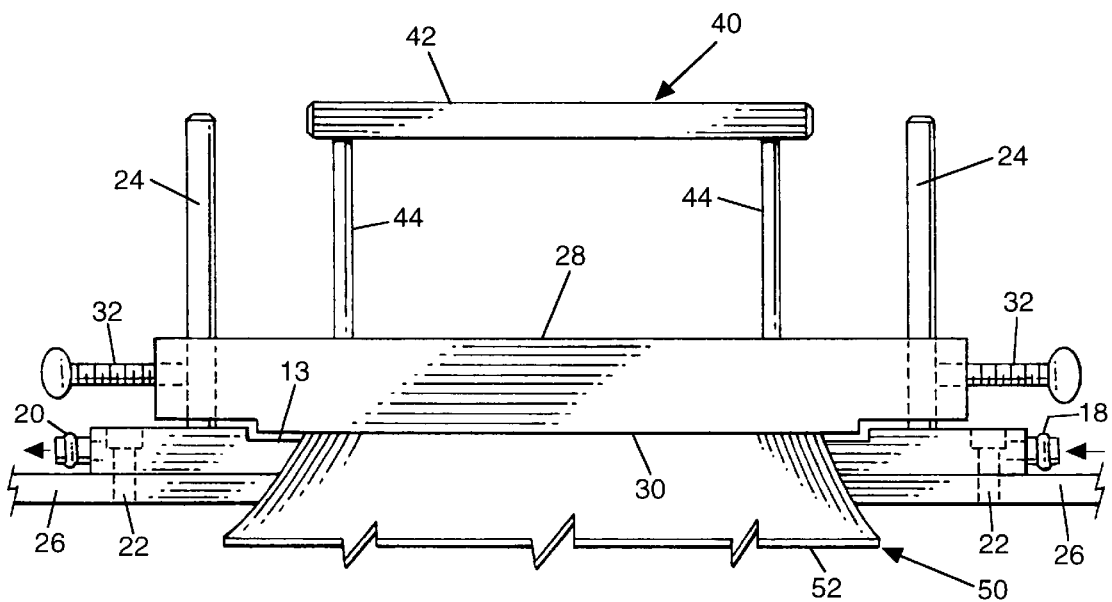
FIG. 3 is a front elevation view of the mold used to form the fiber bundles according to this invention.

FIG. 3 is a side plan view of the mold assembly showing the location of a bundle of fibers in position within the mold when the stabilizing bar 28 is in its clamping position. Also shown are the inlet and outlets for the coolant liquid, 18 and 20.

Figure 4:
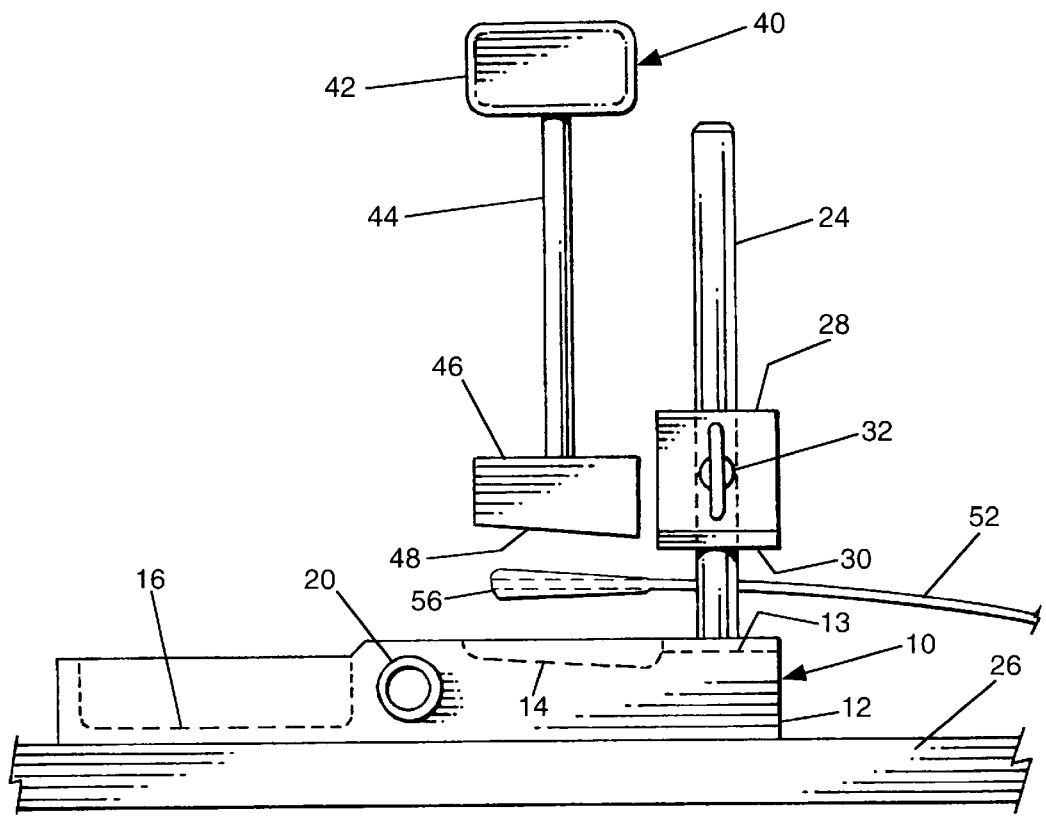
FIG. 4 is an enlarged side elevation view of the mold used to form the fiber bundles according to this invention.

FIG. 4 is a side elevation view of the mold showing a finished bundle of fibers including cured binding composition 56 affixed to the end portion of the fiber bundle as desired.

Figure 5:
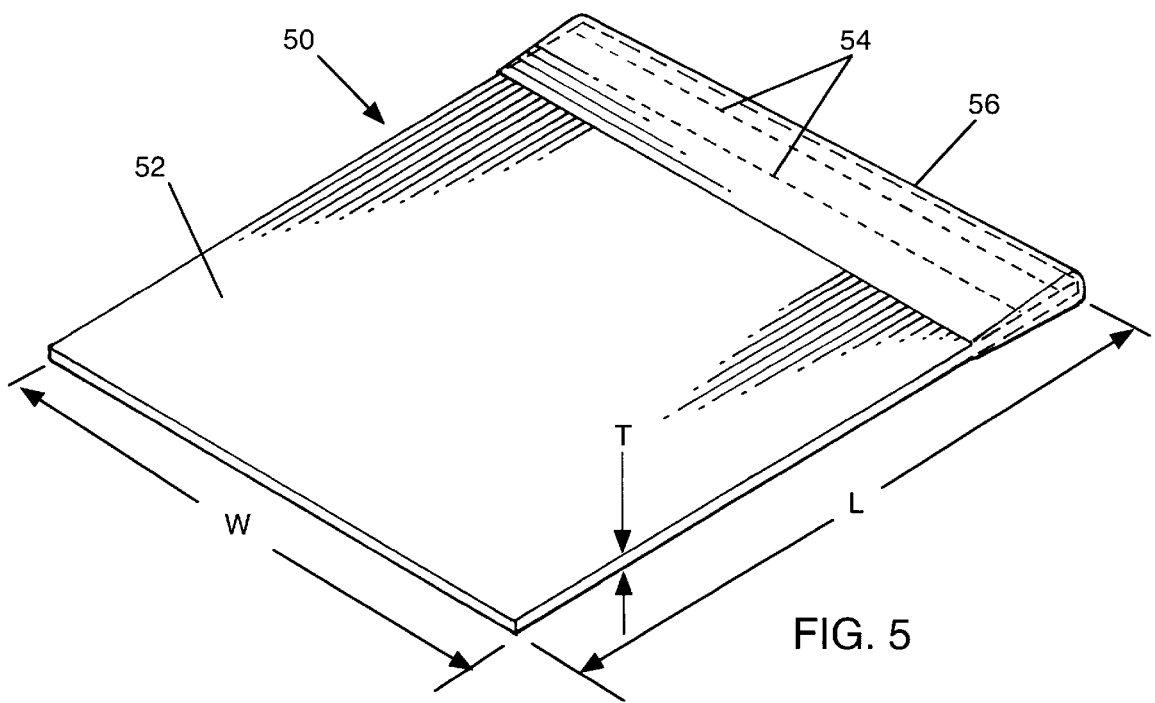
FIG. 5 is a perspective view of a sample of a finished bundle of fibers produced in accordance with the instant invention.

FIG. 5 shows a finished fiber bundle having thickness (T), length (L) and width (W). The stitched portion is protected beneath a bead of binding composition.

To produce a bundle of fibers according to the instant invention, one first positions a bundle of fibers in an adjacent configuration, and then stitches the fibers together as previously indicated. Next, the stitched portion of the fibers is placed into machined recess 14. Then, stabilizing bar 28 is lowered into position as shown in FIG. 3 and held there by the force of screws 32 turned inward against locator rods 24. Next, molten binding composition is poured onto the stitched end portion of the fiber bundle and press bar angled portion 46 is pressed downward onto the stitched portion of the fibers. By virtue of the coolant liquid, which is preferably water, but may comprise glycols, alcohols or brine, and may include corrosion inhibitors as are well known to those skilled in the art. Once the binding composition has solidified, the press bar is removed, the stabilizing bar is raised and the finished fiber bundle is removed from the mold. Trimming with scissors to remove flashings may be undertaken to provide a more aesthetically appealing product.

Fiber bundles produced in such fashion are ideal for physical testing of the fibers for reasons already set forth herein.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. Accordingly, the presently disclosed invention is intended to cover all such modifications and alterations, and is limited only by the scope of the claims which follow.

I claim:

1. A fiber bundle produced by a process which comprises:
   a) providing a plurality of fibers in an essentially planar configuration such that at least one of the ends of said fibers are substantially aligned with one another;
   b) stitching said fibers together in a direction perpendicular to the length dimension of said fibers to produce a stitched fiber composite;
   c) securing said stitched fiber composite in a mold; and
   d) contacting the stitched portions of said fibers with a binding composition so as to produce a finished fiber bundle,
   wherein said binding composition includes a plasticizer.

2. A fiber bundle produced according to claim 1 wherein the thickness (T) of said bundle is in the range of about one fiber diameter to 1.5 centimeters.

3. A fiber bundle produced according to claim 1 wherein the linear density of said finished fiber bundle is in the range of about 50 to 400 strands of fiber per centimeter.

4. A fiber bundle produced according to claim 1 wherein said stitiching is located within about 3 centimeters from the ends of said fibers.

5. A fiber bundle consisting essentially of:
   i) a plurality of fibers arranged in a substantially planar configuration wherein said fibers are oriented essentially parallel to one another, said fibers having at least one of their ends substantially aligned with one another, and comprising stitching in a direction perpendicular to the fiber length dimension; and
   ii) a binding agent disposed on the stitching, wherein said binding agent includes a plasticizer.

6. The fiber bundle of claim 5 wherein said plasticizer is selected from the group consisting of: branched esters of phthalic acid, wax, and beeswax.

7. The fiber bundle of claim 5 wherein said fibers are human hair and said stitching is located within about one inch of the ends of said fibers.

8. A fiber bundle according to claim 5 wherein said fibers are human hair.

9. The fiber bundle of claim 8 wherein said binding agent includes at least one material selected from the group consisting of: polyethylene, polypropylene, polyacrylates, polystyrene, substituted polystyrenes, polyurethanes, ABS, nylons, polybutene, natural latex, polymers and "hot melt" glue.

10. The fiber bundle of claim 8 wherein said binding agent includes at least one material selected from the group consisting of: vinyl acetate polymers, branched esters of phthalic acid, wax, and beeswax.

* * * * *